(12) United States Patent
Tjäder et al.

(10) Patent No.: US 10,238,531 B2
(45) Date of Patent: Mar. 26, 2019

(54) THERMOPLASTIC POLYURETHANES, USE OF THESE MATERIAL FOR THE PREPARATION OF T-FRAMES FOR INTRAUTERINE SYSTEMS AND T-FRAMES MADE OUT OF THIS MATERIAL

(71) Applicant: BAYER OY, Turku (FI)

(72) Inventors: Taina Tjäder, Piispanristi (FI); Nina Stenroos, Turku (FI); Christian Wamprecht, Neuss (DE); Wolfgang Kaufhold, Köln (DE)

(73) Assignee: Bayer Oy, Turku (FI)

( * ) Notice: Subject to any disclaimer, the term of this patent is extended or adjusted under 35 U.S.C. 154(b) by 0 days.

(21) Appl. No.: 15/533,860

(22) PCT Filed: Dec. 4, 2015

(86) PCT No.: PCT/EP2015/078608
§ 371 (c)(1),
(2) Date: Jun. 7, 2017

(87) PCT Pub. No.: WO2016/091730
PCT Pub. Date: Jun. 16, 2016

(65) Prior Publication Data
US 2017/0333246 A1    Nov. 23, 2017

(30) Foreign Application Priority Data

Dec. 8, 2014    (EP) .................................... 14196790

(51) Int. Cl.
| | | |
|---|---|---|
| *A61F 6/14* | (2006.01) | |
| *C08G 18/66* | (2006.01) | |
| *C08G 18/73* | (2006.01) | |
| *C08G 18/22* | (2006.01) | |
| *C08G 18/24* | (2006.01) | |
| *C08G 18/28* | (2006.01) | |
| *C08G 18/32* | (2006.01) | |
| *C08G 18/44* | (2006.01) | |
| *C08K 3/30* | (2006.01) | |

(52) U.S. Cl.
CPC .............. *A61F 6/14* (2013.01); *C08G 18/227* (2013.01); *C08G 18/24* (2013.01); *C08G 18/2825* (2013.01); *C08G 18/3206* (2013.01); *C08G 18/44* (2013.01); *C08G 18/664* (2013.01); *C08G 18/73* (2013.01); *C08G 2125/00* (2013.01); *C08K 2003/3054* (2013.01)

(58) Field of Classification Search
USPC ................... 528/44, 58, 59, 80, 85; 525/467
See application file for complete search history.

(56) References Cited

U.S. PATENT DOCUMENTS

| | | |
|---|---|---|
| 5,374,704 A | 12/1994 | Mueller et al. |
| 9,999,592 B2 * | 6/2018 | Duesterberg ......... A61K 9/0039 |
| 2003/0013792 A1 | 1/2003 | Muhlfeld et al. |

FOREIGN PATENT DOCUMENTS

WO    2011/039418    4/2011

OTHER PUBLICATIONS

Int'l Search Report for PCT/EP2015/078608, three pages dated Mar. 29, 2016.
Written Opinion of ISA for PCT/EP2015/078608, six pages, dated Mar. 29, 2016.

* cited by examiner

*Primary Examiner* — Terressa Boykin
(74) *Attorney, Agent, or Firm* — Nixon & Vanderhye P.C.

(57) ABSTRACT

The present invention relates to a novel thermoplastic polyurethane (TPU) elastomer, T-frames made thereof as well as the use of the new TPU in manufacturing of T-frames for intrauterine systems for contraception and therapy.

20 Claims, 8 Drawing Sheets

Mechanical properties of the thermoplastic polyurethane (TPU) materials of the examples 1 to 10

| TPU material example # | 1 | 2 | 3 | 4 | 5 | 6 | 7 | 8 | 9 | 10 |
|---|---|---|---|---|---|---|---|---|---|---|
| MVR (5 min/10 kg/200 °C) [ml/10 min] | 47,3 | 17,6 | 30,3 | 2,4 | 37,9 | 52,2 | 53,8 | 51,4 | 46,7 | 5,8 |
| Hardness Shore D | 45 | 46 | 44 | 45 | 47 | 48 | 52 | 47 | 48 | 51 |
| Elongation at break [%] | 546 | 436 | 527 | 482 | 558 | 607 | 541 | 456 | 566 | 481 |
| Tensile strength [MPa] | 38,0 | 31,4 | 36,8 | 40,9 | 33,6 | 37,0 | 33,5 | 24,4 | 24,3 | 24,2 |
| Tensile 10% [MPa] | 6,4 | 6,8 | 5,0 | 5,0 | 7,9 | 8,6 | 10,9 | 6,5 | 6,7 | 9,5 |
| Tensile 20% [MPa] | 9 | 9,6 | 7,6 | 7,9 | 10,5 | 11,3 | 14,0 | 9,1 | 9,5 | 12,0 |
| Tensile 50% [MPa] | 12,5 | 13,3 | 11,7 | 12,9 | 13,3 | 13,9 | 16,5 | 12,1 | 12,5 | 14,1 |
| Tensile 100% [MPa] | 14,9 | 16 | 16,2 | 18,2 | 14,9 | 15,3 | 17,3 | 14,6 | 13,7 | 15,0 |
| Tensile 300% [MPa] | 21,8 | 23,2 | 26,7 | 31,6 | 19,6 | 19,7 | 21,3 | 20,6 | 17,4 | 18,5 |
| Flexural e-modulus [MPa] | 109 | 117 | 102 | 92 | 145 | 150 | 203 | 136 | 136 | 202 |

Table 1

Fig. 1

Mechanical properties of the TPU materials of the comparison examples 2 and 3 as disclosed in WO2011/039418 at RT

| TPU material | Example 2 | Example 3 |
|---|---|---|
| MVR (5 min/10 kg/200 °C) [ml/10 min] | 13,5 | 50 |
| Shore D | 43 | 46 |
| Elongation at break [%] | 580 | 524 |
| Tensile strength [N/mm²] | 34 | 27 |
| Tensile 10% [N/mm²] | 5,4 | 6,4 |
| Tensile 20% [N/mm²] | 7,5 | 8,7 |
| Tensile 50% [N/mm²] | 10,2 | 11,2 |
| Tensile 100% [N/mm²] | 12,6 | 12,6 |
| Tensile 300% [N/mm²] | 18,8 | 17,1 |
| Rebound [%] | 51 | 40 |
| Flexural E-modulus [N/mm²] | 88 | 100 |

Table 2

Fig. 2

THERMOPLASTIC POLYURETHANES, USE OF THESE MATERIAL FOR THE PREPARATION OF T-FRAMES FOR INTRAUTERINE SYSTEMS AND T-FRAMES MADE OUT OF THIS MATERIAL

This application is the U.S. national phase of Int'l Application No. PCT/EP2015/078608, filed 4 Dec. 2015, which designated the U.S. and claims priority to Application No. EP 14196790.1, filed 8 Dec. 2014; the entire contents of each of which are hereby incorporated by reference.

FIELD OF THE INVENTION

The present invention relates to novel thermoplastic polyurethanes containing 1,8 Octanediol, 1,10 Decandiol or 1,12 Dodecandiol as chain extenders, the use of these material for the preparation of T-frames for Intrauterine Systems and T-frames made out of this material.

BACKGROUND OF THE INVENTION

The history of Intrauterine Devices (IUDs) dates back to the early 1900s. The first IUD was developed by the German physician, Dr. Richter of Waldenburg. His device was made of silkworm gut and was not widely used[1].

[1] Thiery, Michel (March 1997). "Pioneers of the intrauterine device". *European Journal of Contraception and Reproductive Health Care* 2 (1): 15-23.

Dr. Ernst Gräfenberg, another German physician created the first Ring IUD, Gräfenberg's ring, made of silver filaments.

Dr. Jack Lippes helped begin the increase of IUD use in the United States in the late 1950s. In this time, thermoplastics, which can bend for insertion and retain their original shape, became the material used for first-generation IUDs. Lippes also devised the addition of the monofilament nylon string, which facilitates IUD removal. His trapezoid shape Lippes Loop IUD became one of the most popular first generation IUDs.

In the following years, many different shaped plastic IUDs were invented and marketed including Dalkon Shield, whose design caused bacterial infection and led to thousands of lawsuits. Although the Dalkon shield was removed from the market, it had a lasting, negative impact on IUD use in the United States[2].

[2] Thiery M (June 2000), "Intrauterine contraception: from silver ring to intrauterine contraceptive implant", Eur. J. Obstet. Gynecol. Reprod. Biol. 90 (2): 145-52

The invention of the copper IUD in the 1960s brought with it the capital T-shaped design used by most modern IUDs. U.S. physician, Dr. Howard Tatum determined that the T-shape would work better with the shape of the uterus, which forms a T when contracted. He predicted this would reduce rates of IUD expulsion[1].

Together, Tatum and Chilean physician Jaime Zipper discovered that copper could be an effective spermicide and developed the first copper IUD, TCu200. Improvements by Dr. Tatum led to the creation of the TCu380A (ParaGard), which is currently the preferred copper IUD[1].

The hormonal IUD (respectively Intrauterine Systems, IUS) was also invented in the 1960s and 1970s; initially the goal was to mitigate the increased menstrual bleeding associated with copper and inert IUDs. The first model, Progestasert, was conceived of by Dr. Antonio Scommengna and created by Dr. Tapani J. V. Luukkainen, but the device only lasted for one year of use[2]. Progestasert was manufactured until 2001[3].

[2] Thiery M (June 2000), "Intrauterine contraception: from silver ring to intrauterine contraceptive implant", Eur. J. Obstet. Gynecol. Reprod. Biol. 90 (2): 145-52
[3] Smith (pseudonym), Sydney (Mar. 8, 2003). "Contraceptive Concerns". *medpundit: Commentary on medical news by a practicing physician.* Retrieved 2014-01-16

Three commercial hormonal IUSs are currently available on the market which are: Mirena®, which was also developed by Dr. Luukkainen and released in 1976, Jaydess® which is on the market since 2013 and Levosert® which is marketed in Belgium in the indication Heavy Menstrual Bleeding since 2014.

All market products is in common that the active compound released from the capsule is Levonorgestrel and that the frame on which the capsule is mounted is T-shaped.

In terms of safety and contraceptive efficacy today's intrauterine systems have reached a very high standard.

Although the use of modern IUSs can be considered basically as safe and efficient in rare cases the following side effects are reported:
- abdominal pain,
- infection,
- irregular bleeding,
- hormonal side effects,
- uterine perforation (usually during the insertion procedure),
- cervical laceration,
- septic abortion,
- ectopic pregnancy,
- in some rare cases breaking of the frame,
- pain and difficulties in insertion and/or in removal of the device and
- expulsion of the IUS.

The current invention relates essentially to the last three of the a.m. side effects, which correlate to the mechanical properties of the frame, namely to an improvement of the expulsion rate, avoidance of frame breaking, a better wearing comfort and easier (less painful) removal procedure.

Expulsion rates (besides irregular bleeding in the initial phase of the wearing period, infection and uterine perforation during insertion) is the most common side effect. In the literature a range from 2.2% to 11.4% of users from the first year to the 10th year are reported[4].

[4] Kaneshiro B, Aeby T (2010). "Long-term safety, efficacy, and patient acceptability of the intrauterine Copper T-380A contraceptive device". *International Journal of Women's Health* 2: 211-220

To improve the expulsion rate various approaches have been followed. Most of them relate to dimensions and design of the frame. Thus many approaches try to overcome the problem of expulsion by varying the shape of the frame. A large number of systems which contain essentially a continuous ring shaped frame are described in the literature. For example U.S. Pat. No. 3,431,906 discloses a diamond shaped frame, U.S. Pat. No. 3,516,403 discloses an isosceles triangle form.

Various rings shaped frames are also disclosed in U.S. Pat. No. 4,200,091 and in Bayer Schering Oy's International Patent Application WO2009/122016 which discloses an intrauterine delivery system with a closed continuous frame of a polygonal shape, wherein the drug containing reservoir is connected to the inner surface of the frame.

Even a ball shape frames have been proposed to improve expulsion rate. Thus WO 2010/082197 disclose a Copper based IUD, whereby the frame is made of a memory shape Nickel-Titanium alloy (NiTiNol®) wire, which returns into its original ball shape if released from the inserter tube.

U.S. Pat. No. 4,721,105 (Wildermesch) proposes to anchor the IUS with a thread in the uterus muscle to avoid expulsion in women, in particular in the immediate postpartum period.

Other approaches propose to reinforce and/or to give additional flexibility and/or strength/to the frame by integrating a supporting means into the frame. For example Bayer Schering Oy patent application WO2009/122016 proposed to add supporting means to the frame in a form of a core, fibre or wire. These supporting means can be made of any material which is inert and biologically compatible as long as it possesses sufficient strength and elasticity and remains unchanged for a sufficient period of time in the conditions prevailing in the uterus.

In addition to dimensions and design characteristics, frame material properties are important for an ideal intrauterine system. If no supporting means should be integrated into the frame, it is important that the polymer material as such shows already the required properties. Here besides breaking forces (tensile strength), and memory (ability of the T-frame to return to its original form after release from the insertion tube), flexibility/stiffness of the frame are further key parameters.

Flexibility/stiffness of the frame is particularly important for enhancing wearing comfort or reducing pain during removal of the intrauterine system. In combination with the frame design, memory effect and flexibility can be of relevance also with regard to expulsion.

Unfortunately to a certain extend the a.m. parameters behave in opposite directions, in other words materials with a high stiffness are not flexible enough and materials with a high flexibility do not show the required stiffness.

It is furthermore of importance that the material maintains its mechanical properties in vivo over the wearing period of up to 5 years. Thus a number of materials lose their stiffness at body conditions due to higher temperature (37° C.) and swelling in a humid environment (softening effect in the body/uterus). Also the breaking force of the material can vary over the wearing time due to oxidative or hydrolytic degradation. In the context of the current invention materials' biostability has been tested according to ISO 10993 Part 13 test method.

Last but not least for an in-vivo application biocompatibility has to be considered as a further important factor. Although many polymers are well tolerated and show a high stability in-vivo, e.g. some Polyurethanes have shown a genotoxic effect in animal tests.

Thus selection of a suitable material is by far an easy task. In principle a large number of frame materials had been described in the literature, for example in the International Patent application WO2004/26196 i.a. polyethylene, polypropylene, polymethylpentene ethylene/propylene copolymers, ethylene/ethyl acrylate copolymers, ethylene/vinyl acetate copolymers, polycarbonate, polytetrafluoroethylene (PTFE), fluoroethylenepropylene (PEP), polyvinylidene fluoride (PVDF), polyvinylacetate, polystyrene, polyamides, polyurethane, polybutadiene, polyisoprene, chlorinated polyethylene, polyvinyl chloride, vinyl chloride copolymers with vinyl acetate, poly(methacrylate), polymethyl (meth)acrylate, poly(vinylidene) chloride, poly(vinylidene) ethylene, poly(vinylidene) propylene, polyethylene terephthalate, ethylene vinylacetate, a polyhydroxy alkoanate poly(lacticacid), poly(glycolic acid), poly(alkyl 2-cyanoacrylates), polyanhydrides, polyorthoesters, ethylene/vinyl alcohol copolymer, ethylene/vinyl acetate/vinyl alcohol terpolymer; ethylene/vinyloxy-ethanol copolymer, hydrophilic polymers such as the hydrophilic hydrogels of esters of acrylic and methacrylic acids, modified collagen, cross-linked polyvinyl alcohol, cross-linked, partially hydrolyzed polyvinyl acetate, silicone elastomers, especially the medical grade polydimethyl siloxanes, polyvinylmethylsiloxanes, other organopolysiloxanes, polysiloxane, neoprene rubber, butyl rubber, epichlorohydrin rubbers, hydroxyl-terminated organopolysiloxanes of the room temperature vulcanizing type which harden to elastomers at room temperature following the addition of cross-linking agents in the presence of curing catalysts, two-component dimethylpolysiloxane compositions which are platinum catalysed at room temperature or under elevated temperatures and capable of addition crosslinking as well as mixtures thereof had been disclosed as suitable frame materials.

WO 2011/039418 (Bayer Schering Pharma Oy) discloses ring shaped frames made of thermoplastic polyurethane elastomer. A large number of polyurethane based polymers are disclosed in this application. These polymers are obtainable from a polycarbonate polyol or a mixture of a polycarbonate polyol and a polyether and/or polyester polyol, 1,6-hexamethylene diisocyanate and optionally additional (cyclo)aliphatic diisocyanates and at least one difunctional chain extender. As chain extenders a mixture of a straight chain oligomer, prepared from 1,6-hexanediol and ε-caprolactone, and hydroquinone bis(2-hydroxyethyl)-ethers are disclosed. Preferred chain extenders are long chain aliphatic diol, such as 1,10-decanediol or 1,12-dodecanediol.

It has to be noted that not only the selection of the chain extender influences the material properties but in particular the amount/ratio of the different compounds used for the preparation of the TPU polymer. Thus it has been surprisingly found that the ratio of the different compounds is a key element to achieve a material with does not change its material properties when used in-vivo.

The wide range of polymers disclosed in the a.m. application (WO 2011/039418) are suitable for ring shaped frames. However, as described below in more detail, only a small selection of these polymers is suitable for T-frames. Thus in general ring shaped frames show a higher stiffness due to their closed structure compared to the open form structure in T-frames. Therefore, stiffness is less critical in ring shaped frames.

In addition to the a.m. polymers also biodegradable polymers have been proposed in the literature, e.g. in EP 0873751 (Takeda Chemical Industries). This patent application discloses a biodegradable IUD, wherein an active agent is dispersed in a biodegradable polymer which is mould to a predetermined shape of a ring. Said IUD does not comprise separate frame and reservoir structures.

However, biodegradable polymers can be used only for contemporary supporting means and are therefore rather used for therapeutic indications than for contraception.

Also metal based frames are known, e.g. as described in the a.m. International Application WO 2010/082197, which discloses a memory shape Nickel-Titanium alloy wire as frame material.

Currently the most common T-frame material is polyethylene (PE) as is offers a good compromise between all relevant parameters (flexibility; stiffness; memory effect/rebound; breaking force) and essentially maintains the properties in an in-vivo environment (humidity and at body temperature) over the whole wearing period. Thus it is of no surprise that the current market products Mirena® and Jaydess® use polyethylene based frames. Usually Barium-Sulfate is added to the polymer to enhance X-ray visibility.

However, as the known and used materials (incl. PE) have their strength and weaknesses, the search for an optimal polymer is an ongoing and unsolved problem.

The a.m. Bayer Schering Pharma Oy patent application WO2011/039418(A1) discloses intrauterine systems comprising a flexible, elastic continuous frame comprising a thermoplastic polyurethane elastomer (TPU) and a reservoir with the active substance connected to the frame. The disclosed TPU elastomers show similar properties as the commonly used Polyethylene (PE) but are twice more flexible (soft) than PE. In particular they show a much higher tensile strength (less breaks in use) as it could be proven in various comparison tests.

Also with respect to the influence of temperature and humidity TPU is advantageous as it could be shown in our comparison (see FIG. 3/8). In this experiment material behaviour at body conditions +37° C./wet was mimiced by immersing the samples into Ringer physiological solution for 7 and 21 days and then immediately determining elastic modulus by DMA (Dynamic-Mechanical-Analysis).

Useful thermoplastic polyurethanes and thermoplastic polyurethane elastomers are also disclosed in WO 2009/122016 (Bayer Schering Pharma Oy application). Such materials are commercially available and include polyurethane copolymers, such as block and random copolymers that are polyether based, polyester based, polycarbonate based, aliphatic based, aromatic based and mixtures thereof. Examples of such polymers are known under the trade names Carbothane®, Tecoflex®, Tecothane®, Tecophilic®, Tecoplast®, Pellethane®, Chronothane® and Chronoflex®.

In conclusion TPU's appear to be a good alternative for PE. However, as mentioned above, only a selection of the wide variety of the TPU materials known in the literature can be used for the manufacture of T-frames. Thus the majority of the TPU's disclosed in WO2011/039418 A1 unfortunately change their mechanical properties under in-vivo conditions; in particular the temperature effect on stiffness is significant. Thus a softening occurs in vivo at temperatures around 37° C. and in the wet environment of the uterus.

This is less critical for frames as disclosed and claimed in the above mentioned International Patent application, as these frames have a continuous closed ring shape, which show a certain stability respectively stiffness due to their closed design. However, for an open T-frame design the known thermoplastic polyurethanes are less suitable, as the material stiffness is not sufficient at body temperature.

OBJECT OF THE INVENTION

Therefore, it is an object of the present invention to selection TPUs, with an improved flexibility and stiffness, in particular after exposure to temperature and moisture as present in in-vivo conditions.

It is in particular an object of the present invention to find TPU's where no or only a negligible temperature effect on the material stiffness is observed and which are thus superior to PE.

A further object of the invention is the use of such TPU materials for the manufacturing of T-frames.

A further object of the invention is T-frames for Intra-uterine Systems made of such TPU.

Suitable TPU's should furthermore show a high resistance against hydrolysis, in particular under in-vivo conditions. They should show no of oligomers to the surface of the polymer. This effect is observed if short chain diols, such as 1,4-Butanediol, is used, as these diols could react with hexamethylendiisocyanat to form ring-shaped urethanes which can migrate to the surface of the polymer material.

Furthermore, the use of TPU's based on aromatic diisocyanates should be avoided, as such aromatic diisocyanate based TPU's could partially decompose with moisture to aromatic Diamines which are known to be toxic.

DETAILED DESCRIPTION OF THE INVENTION

Mechanical Testing of Frames/Materials

The mechanical properties of the intrauterine systems, and especially of the frame, must ensure optimal uterine compatibility and user acceptability. If the stiffness and mechanical strength is too low, the system could either be expulsed from the uterus or be prone to rupture. If the stiffness and mechanical strength is too high, the inflexibility of the device could cause irritation or ulceration of the uterine tissue. Therefore, the mechanical characteristics (breaking force, stiffness/flexibility and memory/rebound of the material) were assessed by using standard methods of compressing, described in the literature.

These physical parameters can be considered as surrogate parameters with regard to expulsion, wearing comfort and comfort/pain during insertion and removal of the device, capability and speed of the T-frame to return to its original shape after being released from the insertion tube and reduction of the risk of breaking during usage.

Memory is measured for characterising the ability of a frame to recover its shape after acute compaction.

Stiffness/flexibility is tested for characterizing the property of a frame to resist low and moderate short term deformation. Thus flexibility can be correlated with wearing comfort and comfort during use/removal. Flexibility in connection with the shape of the frame furthermore correlates to the risk of expulsion.

Breaking force/tensile strength goes along with the risk of breaking when the device is in use.

The following nomenclature has been used in the context of this invention. Respective physical in-vitro parameters have been correlated to a clinical effect.

Definitions:

| Physical parameter | Testmodel | Clinical relevance |
| --- | --- | --- |
| Flexibility/Stiffness | Flexural/bending Modulus | Expulsion, wearing comfort and pain during removal of the T-frame from the uterus |
| Memory effect | Frame is collapsed for 5 min, it is released and let to recover for 1 min the unrecovered portion is determined as degrees. | Expulsion and Insertion time (how fast does the frame return into its original shape after release from the insertion tube) |
| Tensile strength/Breaking force | Force needed to achieve an elongation (extension) of 100%/Max load of the frame | Breaking of frame during wearing |

Description of the Test Models:
Test Models to Determine the Mechanical Properties of the TPU The following material testing models have been used to measure the mechanical properties of the TPU materials according to the examples 1 to 10 (see FIG. 1/8, table 1):

Melt Volume Rate (MVR): According to DIN ISO 1133
Hardness: According to DIN 53505

Tensile test for 10%-, 20%-, 50%-, 100%- and 300% tensile, tensile strength and elongation at break: According to DIN 53504

Flexural e-modulus: According to DIN ISO 178

The biostability of the materials was investigated adapting ISO 10993 Part 13 method.

Test Models to Determine the Mechanical Properties of the T-Frames

The following test models have been used to measure the mechanical properties of the T-frames prepared from TPU material according to the examples 1 to 10:

T-frame flexibility/stiffness
has been measured with a test model based on the general principles of the flexural modulus test, which had been adjusted to the design of T-shaped frames.

In our test model the horizontal arms of the T-body have been bended until the weight of 50 grams is achieved, the travel required to achieve a force of 50 grams is reported as a flexibility [mm/50 g]. The stiffer the frame is the less the arms move to achieve the limit weight.

Breaking Force/Tensile Strength
of the frames has been measured analogous to the method established for Cu-IUD's (ISO 7439) by stretching the frame till it breaks. The maximal force is indicated in N.

Memory Effect
The memory effect has been tested analog to the test as it is established for Copper IUDs (ISO 7439).

Although known by a person skilled in the art it should be remarked that the test parameters measured for the T-shaped frames are not only dependent from the material properties but also from the shape of the sample.

Thus when comparing "frame parameters" (as shown in FIG. 5/8) it has to be ensured that frames with an identical shape are compared. Even if the absolute values can differ in dependence from that frame shape, the relative values are comparable and can be used to assess the suitability of the material for its intended use in T-frames.

Opening Force
describes the opening energy/capacity of the frame when being collapsed for certain time. Expansion force is determined and is especially dependent on the material, but also from the frame design.

BRIEF DESCRIPTION OF THE FIGURES

FIG. 1 (Table 1) shows the mechanical properties of the thermoplastic polyurethane (TPU) materials of the examples 1 to 10 according to the current invention. With the exception of the MRV data all data have been measured at room temperature [RT]. The MRV values have been measured at 200° C.

All TPU materials as described in the current invention (examples 1-7) have a flexural e-modulus of >90 MPa). Examples 8-10 (TPU's mixed with 20% $BaSO_4$ have a flexural e-modulus of >102 MPa).

The inorganic filler $BaSO_4$ is added to enhance X-ray visibility but is also known to increase stiffness of polymer material.

Bariumsulfate containing example 8 is based on a TPU prepared according to example 3) and bariumsulfate containing example 9), based on the TPU of example 4.

As explained above the flexural e-modulus value can be regarded as a specific characteristic (surrogate parameter) for frame stiffness/flexibility. According to the present invention TPU materials with a flexural e-modulus value above 90 MPa (N/mm$^2$) at room temperature are suitable for T-frames, whereby this value refers to the basic (pure) TPU without $BaSO_4$ as additive.

TPUs suitable for T-frames compounded with ≥20% Bariumsulfate the e-modulus value should be above 102 MPa at room temperature.

FIG. 2 (Table 2) shows the mechanical properties at room temperature of the thermoplastic polyurethane (TPU) materials of the comparison examples 2 and 3 according to WO2011/039418.

For the unblended TPU as prepared according to comparion example 2, a value below 90 MPa, namely 88 MPa has been measured.

Comparison example 3 of WO2011/039418 refers to a blend of TPU with (20%) $BaSO_4$. A value of 100 MPa has been measured for this composition.

It should be remarked that unblended TPU, as used in comparision example 3, was prepared as described in example 1 of WO2011/039418. For this (example 1) a value of 66 MPa was measured.

Figure 3:
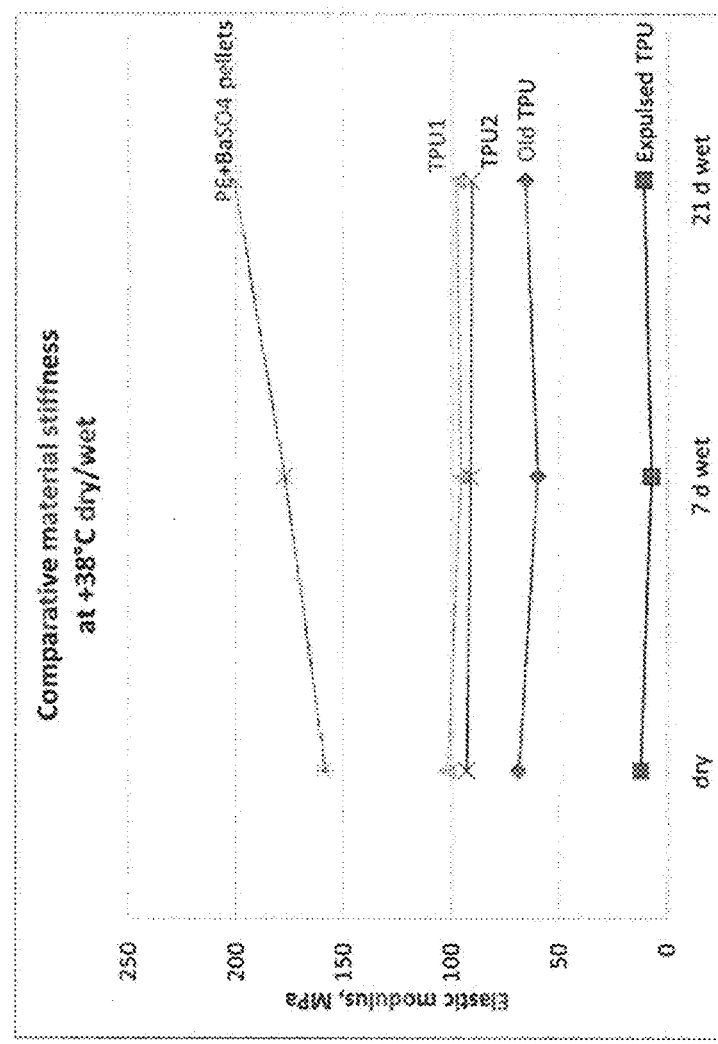

FIG. 3 compares the material stiffness[5] of different frame materials at 38° C. in dependency of exposure with moisture (0 days, vs. 7 and 21 days moisture exposure). It has to be remarked that "dry" in the context of this invention and as used in FIG. 3/8 means a TPU material after exposure to air. This material contains ~1% water.

[5]Stiffness is the counterpart to flexiblility. If material aren't flexibile it is stiff and visa versa.

In this comparison experiment TPU frames according to the present invention (TPU1 and TPU2), a TPU frame as disclosed in WO2011/039418, Carbothane and Polyethylene/BaSO4 frames have been compared in terms of stiffness/flexibility. It should be remarked that all test materials have been compounded with ~20% $BaSO_4$.

The light blue "star" curve refers to PE/BaSO4 material, the blue "diamond" curve (named "old TPU") refers to a TPU as described in WO2011/039418 (similar to example 3) and the red "square" curve (named as expulsed TPU) refers to an aliphatic Carbothane® containing 20% $BaSO_4$ (Carbothane PC-3595A-BA20).

The green "triangle" curve" (named TPU1) and the violet "cross" curve (named TPU2) refer to the new TPUs according to the invention [TPU1=example 8; TPU2=example 9).

As the data show, TPU's in general are relative insusceptible against moisture in comparison to PE.

However, although the effect of moisture on TPU materials is negligible the old TPU as well as Carbothane® show a stiffness under in-vivo conditions which is too low to be used in T-frames.

Contrary to that the new TPUs according to the invention (examples 8 and 9) show an elastic modulus of 98 MPa at +38° C. in wet medium which is an increase of 48% compared to the TPU as disclosed in WO2011/039418 and an increase of 100% compared to Carbothane® PC-3595A-BA20.

Figure 4:
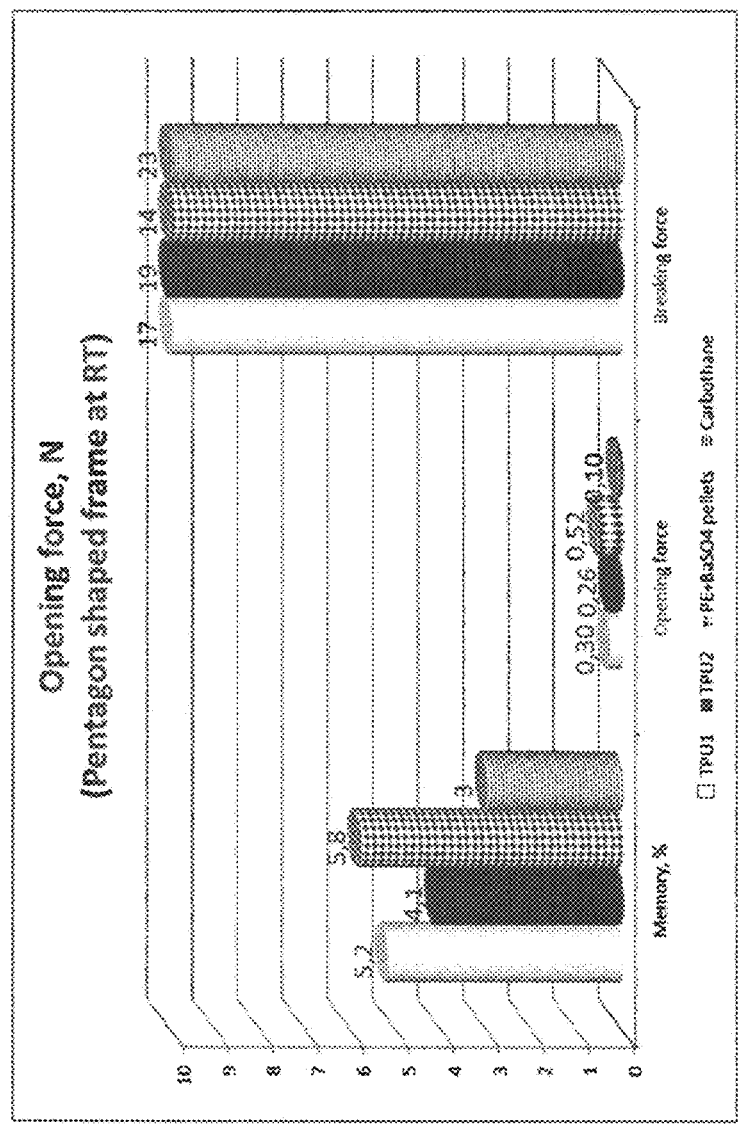

FIG. 4 compares the "Memory Effect", Opening force and "Breaking force" of the different materials. The "dotted" bar gives the values for Polyethylene, the "faciated" bar for a Carbothane®. The "white" and "black" bar shows the data for the TPUs according to the current invention (examples 8 and 9).

The breaking forces for TPU's, in particular for Carbothane® show increased values (23) in comparison to PE (14).

Also the memory effect of the TPU materials is comparable or even better compared to PE (5,8).

Figure 5:
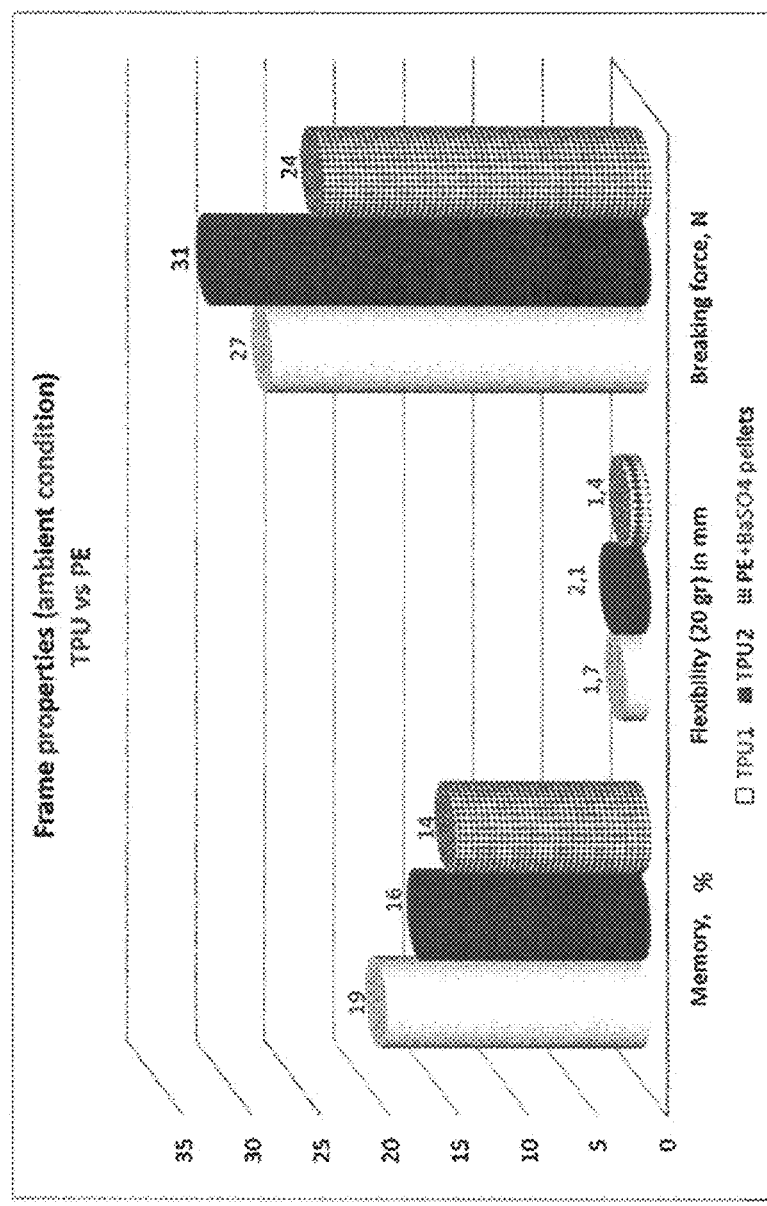

However, it should be remarked that for this comparison experiment closed frames with a pentagon shape have been investigated, thus the data measured for the memory effect have only exploratory character and are not directly transferable to T-frames as the results in FIG. 5 show.

The memory effect reflects the capability of the frame to return into its old shape after the frame is released from the insertion tube.

The opening force of TPU's according to the current invention is compared with PE/BaSO$_4$ respectively Carbothane®. It is a force the frame tries to open up itself back to original shape when being collapsed in to a slot (insertion tube/cervix). The opening force is therefore an important parameter.

In other words, if the frame has a good memory its effect will be lost if the frame has no opening force to "utilize" the good memory in uterine cavity.

This parameter (opening force) is of clinical relevance as this force acts on the cervix channel when the Intrauterine System is removed from the uterus through the cervix channel at the end of its wearing time. Low forces go along with less pain but bear also a higher risk of expulsion during the wearing time of the IUS.

Opening force and Memory has been measured for frames with a pentagon shape, thus the absolute values are not directly transferable to T-frames. However, the ratio between the values of the different materials will remain essentially unchanged, thus although for T-frames lower opening forces and a similar memory as compared to PE can be foreseen.

A relative high opening force is needed for PE (0.52 N) ("dotted" bar in FIG. 4/8), which could cause pain during removal of the IUS.

Carbothane® ("fascinated" bar) shows a value of only 0.1 N which is favorable if the IUS is removed but by far too low to ensure that the IUS is stable fixed in the uterus. Thus high expulsion rates can be expected with this material.

The materials according to the invention show values of 0.3 N ("white" bar; example 8) respectively 0.26 N ("black" bar; example 9), which is a good compromise between comfort during removal and avoidance of expulsion.

The memory effect for the new TPU's according to the invention is lower compared to PE but still in an acceptable range.

FIG. 5 compares the "Memory Effect", Flexibility and "Breaking force" for PE in comparison to the TPU's according to the current invention (examples 8 and 9). The investigations have been made with T-frames. Results are essentially in line with the results as shown in FIG. 4 measured for frames with a closed pentagon shape design. All TPU materials show improved values in terms of flexibility and breaking force in comparison to PE as used in the market products Mirena® and Jaydess®. The memory effect of TPU's is slightly worse compared to Polyethylen (PE). However, as the memory effect has less clinical relevance than flexibility or opening force, this marginal disadvantage is negligible.

Figure 6:
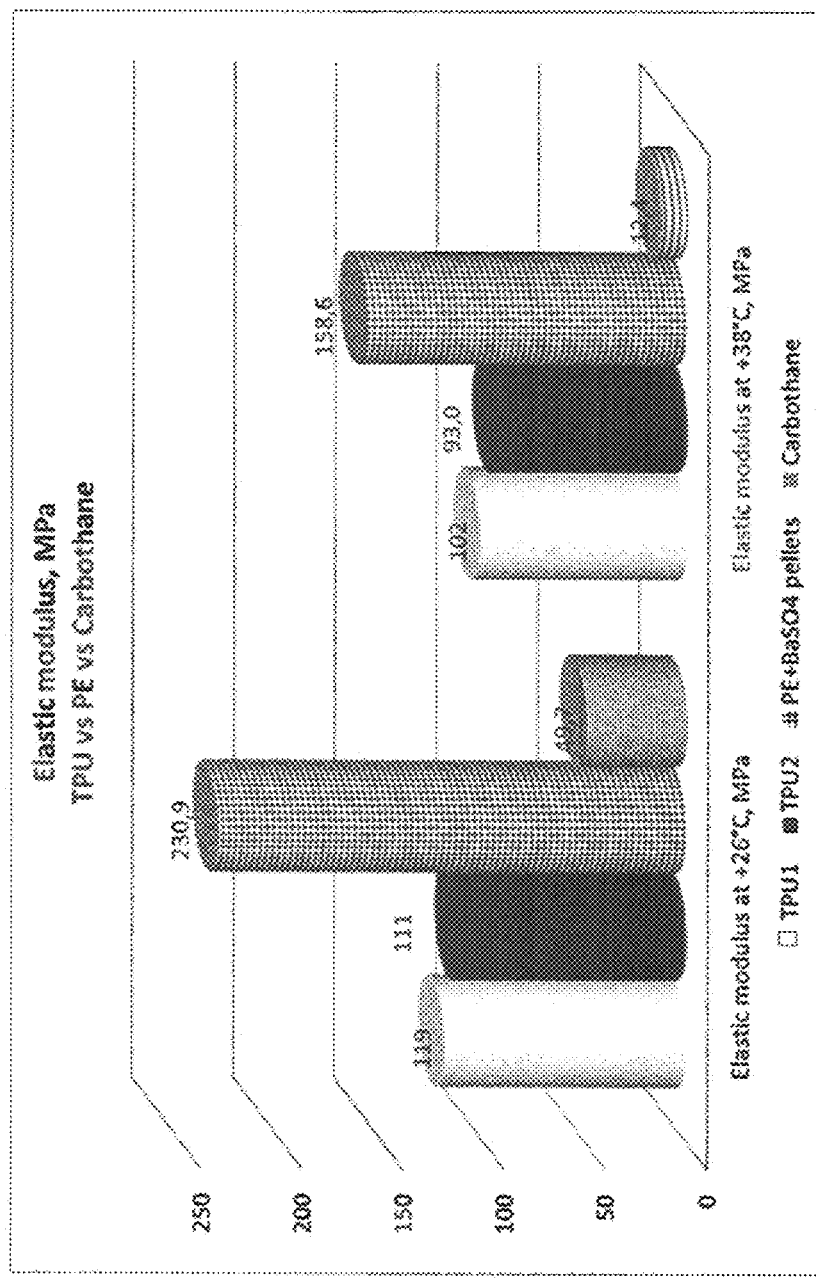

FIG. 6 shows the temperature effect on the elastic modulus of the material. Flexibility/stiffness at room temperature (26° C.) and body temperature (38° C.) have been investigated. Whereby the temperature effect is significant, when looking at PE and Carbothane®, a neglectable effect is observed for the new TPU materials according to the current invention. Although the stiffness is lower as for PE it is still in a range which makes the material eligible for T-frames. The lower stiffness of the TPU according to the current invention results in a better wearing comfort and less pain during removal of the IUS.

Figure 7:
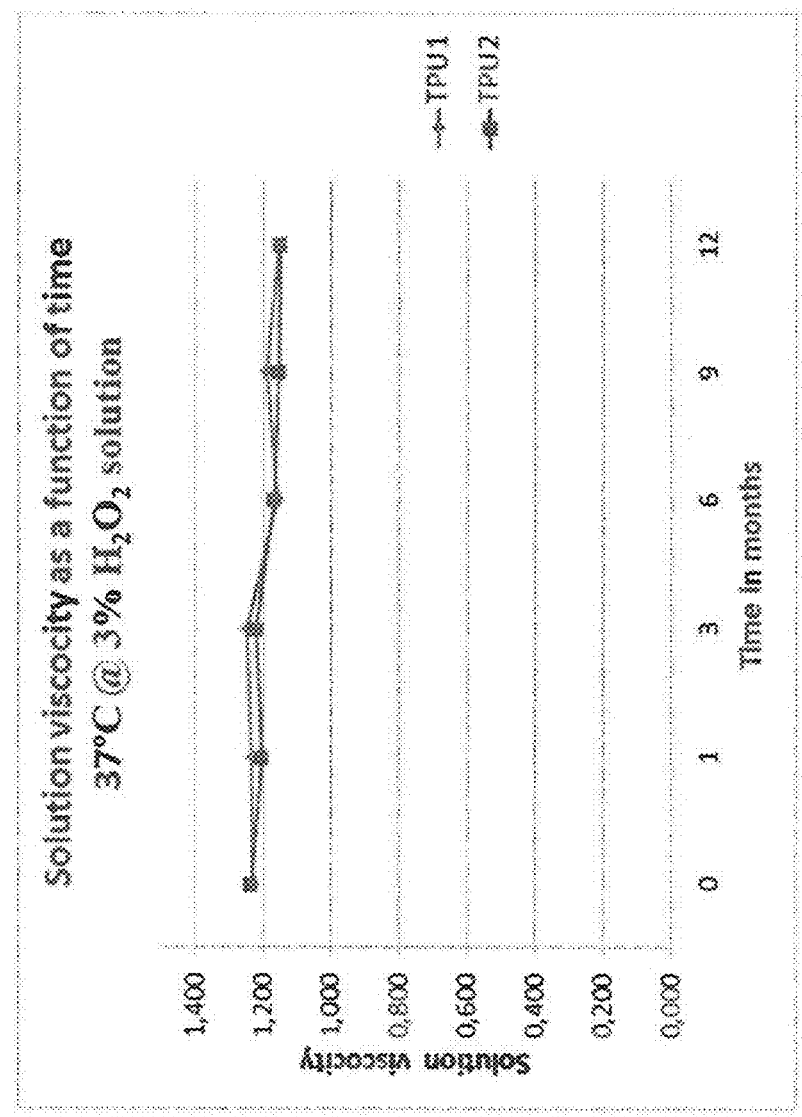
Figure 8:
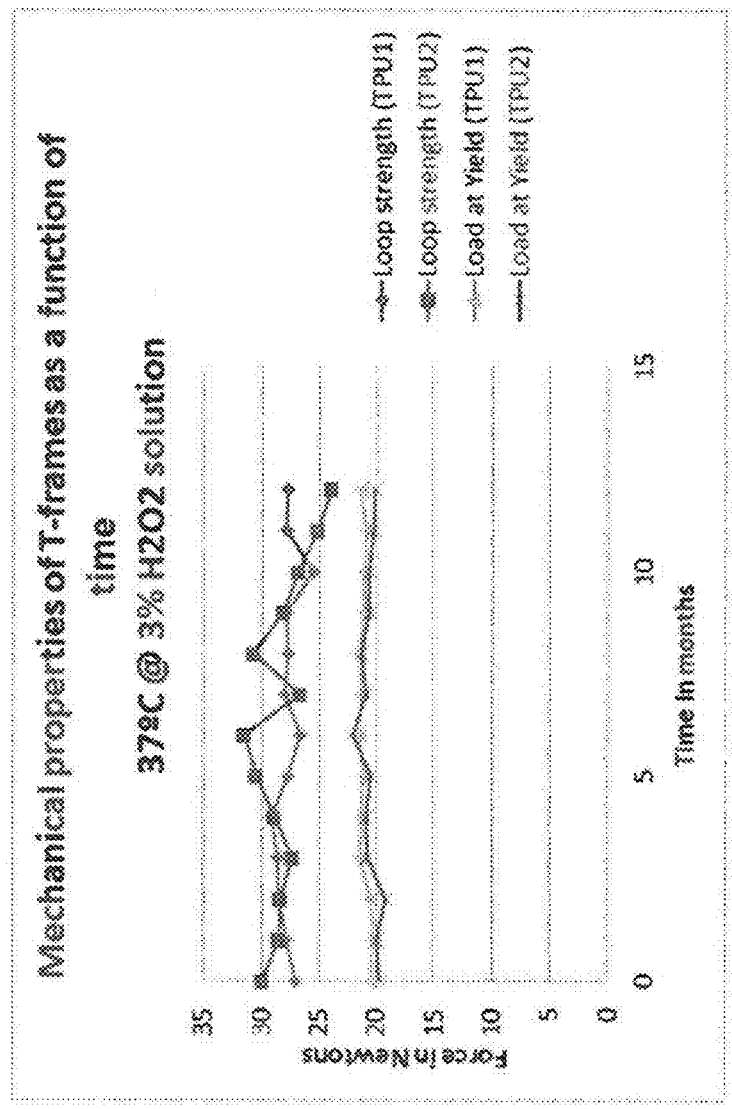

FIG. 7 and FIG. 8 shows the results of the bio stability testing adapted from the ISO 10993 Part 13 method. The physical properties [i.e. solution viscosity (FIG. 7), and mechanical properties (FIG. 8)] were followed as a function of time for 12 months at oxidative condition (3% $H_2O_2$-water solution) and at body temperature. This stressed condition showed that the new materials are biostable.

EXAMPLES

The following examples serve to illustrate the invention.
Abbreviations (used in the examples):
Polycarbonate Diols
DE C 2201: Desmophen® C 2201; Polycarbonate diol based on 1,6-hexanediol with a hydroxyl number of 56 mg KOH/g; product of Bayer MaterialScience AG
DE C XP 2613: Desmophen® C XP 2613; Polycarbonate diol based on 1,4-butanediol and 1,6-hexanediol with a hydroxyl number of 56 mg KOH/g; product of Bayer MaterialScience AG
Isocyanate
HDI: 1,6 Hexamethylen diisocyanate
Chain Extender
HDO: 1,6-Hexanediol
DDO: 1,12-Dodecanediol
Antioxidants
Pentaerythritol tetrakis(3-(3,5-di-tert-butyl-4-hydroxyphenyl)propionate) (Trade name Irganox® 1010; Antioxidant from BASF SE)
2', 3-bis [[3-[3,5-di-tert-butyl-4-hydroxyphenyl]propionyl]]propionohydrazide (Trade name: Irganox® MD 1024; Metal deactivator and primary, phenolic antioxidant from BASF SE)
Catalysts
K-KAT® 348: Bismut catalyst from King Industries Inc.
TIPT: Tetraisopropyltitanate
Additive
Licowax® E: Mould release agent from Clariant GmbH
Inorganic Filler
BaSO$_4$: Bariumsulfate
Chain Terminators (Optionally)
1-Hexanol, 1-Octanol or 1-Decanol Example 1

A mixture of 1001, 79 g DE C 2201, 254.19 g HDO, 5.11 g Irganox 1010 and 1.00 g K-Kat 348 was heated to 110° C., while stirring with a blade agitator at a speed of 500 revolutions per minute (rpm). Following this, 441.86 g HDI was added. The mixture was then stirred until the maximum possible increase in viscosity was obtained, and the TPU was then poured off. The material was thermally post-treated for 30 minutes at 80° C. and then, after cooling to room temperature, granulated.

Example 2

A mixture of 1001, 79 g DE C 2201, 271.93 g EDO, 5.24 g Irganox 1010 and 1.00 g K-Kat 348 was heated to 110° C., while stirring with a blade agitator at a speed of 500 revolutions per minute (rpm). Following this, 466.87 g HDI was added. The mixture was then stirred until the maximum possible increase in viscosity was obtained, and the TPU was then poured off. The material was thermally post-treated for 30 minutes at 80° C. and then, after cooling to room temperature, granulated.

Example 3

A mixture of 1001, 79 g DE C 2201, 303.79 g DDO, 4.94 g Irganox 1010 and 0.70 g TIPT was heated to 125° C., while stirring with a blade agitator at a speed of 500 revolutions per minute (rpm). Following this, 336.00 g HDI was added. The mixture was then stirred until the maximum possible increase in viscosity was obtained, and the TPU was then poured off. The material was thermally post-treated for 30 minutes at 80° C. and then, after cooling to room temperature, granulated. This material was used as base material for example 8.

Example 4

A mixture of 1056, 50 g DEC XP 2613, 354.42 g DDO, 5.38 g Irganox 1010 and 0.74 g TIPT was heated to 125° C., while stirring with a blade agitator at a speed of 500 revolutions per minute (rpm). Following this, 378.0 g HDI was added. The mixture was then stirred until the maximum possible increase in viscosity was obtained, and the TPU was then poured off. The material was thermally post-treated for 30 minutes at 80° C. and then, after cooling to room temperature, granulated. This material was used as base material for example 9.

Example 5

A mixture of 1001, 79 g DE C 2201, 435.43 g DDO, 5.66 g Irganox 1010 and 1.00 g K-Kat 348 was heated to 125° C., while stirring with a blade agitator at a speed of 500 revolutions per minute (rpm). Following this, 442.97 g HDI was added. The mixture was then stirred until the maximum possible increase in viscosity was obtained, and the TPU was then poured off. The material was thermally post-treated for 30 minutes at 80° C. and then, after cooling to room temperature, granulated. This material was used as base material for example 10.

Example 6

A mixture of 1001, 79 g DEC 2201, 465.81 g DDO, 5.83 g Irganox 1010 and 1.00 g K-Kat 348 was heated to 125° C., while stirring with a blade agitator at a speed of 500 revolutions per minute (rpm). Following this, 468.05 HDI was added. The mixture was then stirred until the maximum possible increase in viscosity was obtained, and the TPU was then poured off. The material was thermally post-treated for 30 minutes at 80° C. and then, after cooling to room temperature, granulated.

Example 7

A mixture of 1001, 79 g DE C 2201, 658.21 g DDO, 6.88 g Irganox 1010 and 1.00 g K-Kat 348 was heated to 125° C., while stirring with a blade agitator at a speed of 500 revolutions per minute (rpm). Following this, 625.28 HDI was added. The mixture was then stirred until the maximum possible increase in viscosity was obtained, and the TPU was then poured off. The material was thermally post-treated for 30 minutes at 80° C. and then, after cooling to room temperature, granulated.

Example 8

426.40 g BaSO$_4$, 5.81 g Licowax E and 5.81 g Irganox MD 1024 were added to 1500 g TPU granules prepared according example 3. The mixture was extruded on an extruder of type DSE 25/4Z, 360 Nm, having the following structure:
1. cold intake zone with conveyor elements
2. first heating zone (210° C.) with first kneading zone
3. second heating zone (225° C.) with conveyor elements and second kneading zone
4. third heating zone (225° C.) with kneading zone, conveyor elements and vacuum degassing
5. deflection head (220° C.) and die (220° C.), with a delivery rate of 4.8 kg/h and a speed of 30-40 rpm.

The extrudates were then processed to granules by means of an extrudate granulator and to injection-molded sheets by means of an injection-molding machine.

Example 9

426.40 g BaSO$_4$, 5,81 g Licowax E and 5.81 g Irganox MD 1024 were added to 1500 g TPU granules prepared according example 4. The mixture was extruded on an extruder of type DSE 25/4Z, 360 Nm, having the following structure:
1. cold intake zone with conveyor elements
2. first heating zone (210° C.) with first kneading zone
3. second heating zone (225° C.) with conveyor elements and second kneading zone
4. third heating zone (225° C.) with kneading zone, conveyor elements and vacuum degassing
5. deflection head (220° C.) and die (220° C.), with a delivery rate of 4.8 kg/h and a speed of 30-40 rpm.

The extrudates were then processed to granules by means of an extrudate granulator and to injection-molded sheets by means of an injection-molding machine.

Example 10

426.40 g BaSO$_4$, 5.81 g Licowax E and 5.81 g Irganox MD 1024 were added to 1500 g TPU granules prepared according example 5. The mixture was extruded on an extruder of type DSE 25/4Z, 360 Nm, having the following structure:
1. cold intake zone with conveyor elements
2. first heating zone (210° C.) with first kneading zone
3. second heating zone (225° C.) with conveyor elements and second kneading zone
4. third heating zone (225° C.) with kneading zone, conveyor elements and vacuum degassing
5. deflection head (220° C.) and die (220° C.), with a delivery rate of 4.8 kg/h and a speed of 30-40 rpm.

The extrudates were then processed to granules by means of an extrudate granulator and to injection-molded sheets by means of an injection-molding machine.

The mechanical properties of the thermoplastic polyurethane (TPU) materials of the examples 1 to 10 are presented in FIG. 1/8.

Comparison Examples as Disclosed in WO2011/039418

Comparison Example 1

A mixture of 722.3 g DE C2201, 222.0 g HQEE, 174 g Cap-HDO, 4.5 g Irganox 1010 and 0.7 g K-Kat 348 was heated to 110° C., while stirring with a blade agitator at a speed of 500 revolutions per minute (rpm). Following this, 376.4 g HDI was added. The mixture was then stirred until the maximum possible increase in viscosity was obtained, and the TPU was then poured off. The material was thermally post-treated for 30 minutes at 80° C. and then, after cooling to room temperature, granulated. This material was used as base material for comparison example 3.

Comparison Example 2

A mixture of 954.6 g DE C2201, 249.8 g DDO, 4.5 g Irganox 1010 and 1.0 g K-Kat 348 was heated to 125° C., while stirring with a blade agitator at a speed of 500 revolutions per minute (rpm). Following this, 290.1 g HDI was added. The mixture was then stirred until the maximum possible increase in viscosity was obtained, and the TPU was then poured off. The material was thermally post-treated for 30 minutes at 80° C. and then, after cooling to room temperature, granulated.

Comparison Example 3

385 g $BaSO_4$, 5.25 g Licowax E and 5.25 g Irganox MD 1024 were added to 1355 TPU granules prepared according example 1. The mixture was extruded on an extruder of type DSE 25/4Z, 360 Nm, having the following structure:
1. cold intake zone with conveyor elements
2. first heating zone (210° C.) with first kneading zone
3. second heating zone (225° C.) with conveyor elements and second kneading zone
4. third heating zone (225° C.) with kneading zone, conveyor elements and vacuum degassing
5. deflection head (220° C.) and die (220° C.), with a delivery rate of 4.8 kg/h and a speed of 30-40 rpm.

The extrudates were then processed to granules by means of an extrudate granulator and to injection-molded sheets by means of an injection-molding machine.

The mechanical properties of the thermoplastic polyurethane (TPU) materials of the comparison examples 2 and 3 are presented in FIG. 2/8 (Table 2).

The invention claimed is:
1. A thermoplastic polyurethane elastomer, wherein the elastomer is made of
   a) 1,6-Hexamethylene diisocyanate with a content of 19.5 to 21.5 weight-%,
   b) a polycarbonate diol based on 1,6-Hexane diol with a number average molecular weight between 1900 and 2100 g/mol with a content of 60.0 to 62.00 weight-%,
   c) 1,12-Dodecanediol with a content of 16.5 to 18.5 weight-%,
in the presence of
   e) TIPT catalyst,
with the addition of
   f) $BaSO_4$ in the range of 0 to 35 wt.-%, based on the weight of the thermoplastic polyurethane made of components a) to c),
   g) Pentaerythritol tetrakis(3-(3,5-di-tert-butyl-4-hydroxyphenyl)propionate),
   h) optionally, further additives and/or auxiliary substances.
2. A thermoplastic polyurethane elastomer, wherein the elastomer is made of
   a) 1,6-Hexamethylene diisocyanate with a content of 19 to 21 weight-%,
   b) A polycarbonate diol based on a mixture of 1,4-Butane diol and 1,6-Hexane diol with a number average molecular weight between 1900 and 2100 g/mol with a content of 58 to 60 weight-%,
   c) 1,12-Dodecanediol with a content of 18.8 to 20.8 weight-%,
in the presence of
   e) TIPT catalysts,
with the addition of
   f) $BaSO_4$ in the range of 0 to 35 wt.-%, based on the weight of the thermoplastic polyurethane made of components a) to d),
   g) Pentaerythritol tetrakis(3-(3,5-di-tert-butyl-4-hydroxyphenyl)propionate),
   h) optionally, further additives and/or auxiliary substances.
3. A T-frame for Intrauterine System wherein the frame is made of a thermoplastic polyurethane elastomer according to claim 1.
4. A T-frame for Intrauterine Systems according to claim 3, wherein the T-frame contains locking parts on the vertical stem to hold the capsule with the active compound.
5. A T-frame for Intrauterine Systems according to claim 3, wherein the T-frame contains a metal ring to enhance ultrasound visibility.
6. A method for manufacture of T-frames for Intrauterine System, the method comprising the step of producing a T-frame for Intrauterine System with a thermoplastic polyurethane elastomer according to claim 1.
7. A T-frame for Intrauterine System wherein the frame is made of a thermoplastic polyurethane elastomer according to claim 2.
8. A T-frame for Intrauterine System according to claim 7, wherein the T-frame contains locking parts on the vertical stem to hold the capsule with the active compound.
9. A T-frame for Intrauterine System according to claim 7, wherein the T-frame contains a metal ring to enhance ultrasound visibility.
10. A method for manufacture of T-frame for Intrauterine System, the method comprising the step of producing a T-frame for Intrauterine System with a thermoplastic polyurethane elastomer according to claim 2.
11. A thermoplastic polyurethane elastomer, wherein the elastomer is made of
   a) 336.00 g 1,6-Hexamethylene diisocyanate,
   b) 1001.79 g DE C 2201,
   c) 4.94 g 1,12-Dodecanediol,
in the presence of
   e) 0.7 g TIPT catalyst and 4.94 g Pentaerythritol tetrakis (3-(3,5-di-tert-butyl-4-hydroxyphenyl)propionate),
with the addition of
   f) 426.4 g $BaSO_4$,
   g) 5.81 g 2', 3-bis [[3-[3, 5-di-tert-butyl-4-hydroxyphenyl] propionyl]] propionohydrazide, and
   h) 5.81 g Licowax E®.
12. A T-frame for Intrauterine System wherein the frame is made of a thermoplastic polyurethane elastomer according to claim 11.
13. A T-frame for Intrauterine System according to claim 12, wherein the T-frame contains locking parts on the vertical stem to hold the capsule with the active compound.
14. A T-frame for Intrauterine System according to claim 12, wherein the T-frame contains a metal ring to enhance ultrasound visibility.
15. A method for manufacture of T-frame for Intrauterine System, the method comprising the step of producing a T-frame for Intrauterine System with a thermoplastic polyurethane elastomer according to claim 11.
16. A thermoplastic polyurethane elastomer, wherein the elastomer is made of
   a) 378.0 g 1,6-Hexamethylene diisocyanate,
   b) 1056.50 g DE C XP 2613,
   c) 354.42 g 1,12-Dodecanediol, in the presence of
- e) 0.74 TIPT catalyst and 5.38 g Pentaerythritol tetrakis (3-(3,5-di-tert-butyl-4-hydroxyphenyl)propionate), with the addition of
- f) 426.40 g BaSO$_4$,
- g) 5.81 g 2', 3-bis [[3-[3, 5-di-tert-butyl-4-hydroxyphenyl] propionyl]] propionohydrazide, and
- h) 5.81 g Licowax E®.

17. A T-frame for Intrauterine System wherein the frame is made of a thermoplastic polyurethane elastomer according to claim 16.

18. A T-frame for Intrauterine System according to claim 17, wherein the T-frame contains locking parts on the vertical stem to hold the capsule with the active compound.

19. A T-frame for Intrauterine System according to claim 17, wherein the T-frame contains a metal ring to enhance ultrasound visibility.

20. A method for manufacture of T-frame for Intrauterine System, the method comprising the step of producing a T-frame for Intrauterine System with a thermoplastic polyurethane elastomer according to claim 16.

* * * * *